United States Patent
Noshi

(10) Patent No.: US 6,794,667 B2
(45) Date of Patent: Sep. 21, 2004

(54) SOURCE PIN LOADING METHODS AND APPARATUS FOR POSITRON EMISSION TOMOGRAPHY

(75) Inventor: Hani Ikram Noshi, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 130 days.

(21) Appl. No.: 10/065,584

(22) Filed: Oct. 31, 2002

(65) Prior Publication Data

US 2004/0084638 A1 May 6, 2004

(51) Int. Cl.$^7$ .............................................. G21F 5/02
(52) U.S. Cl. .................................... 250/498.1; 378/9
(58) Field of Search ..................... 250/493.1, 497.1, 250/498.1, 363.03, 363.04, 370.08, 370.09, 505.1, 506.1, 507.1; 378/9

(56) References Cited

U.S. PATENT DOCUMENTS

| | | | |
|---|---|---|---|
| 4,235,454 A | 11/1980 | Gray et al. | |
| 4,501,011 A | 2/1985 | Hauck et al. | |
| 4,791,934 A | 12/1988 | Brunnett | |
| 5,594,638 A | 1/1997 | Iliff | |
| 5,711,297 A | 1/1998 | Iliff | |
| 5,724,968 A | 3/1998 | Iliff | |
| 5,821,541 A | 10/1998 | Tumer | |
| 5,834,780 A | 11/1998 | Morgan et al. | |
| 5,868,669 A | 2/1999 | Iliff | |
| 5,910,107 A | 6/1999 | Iliff | |
| 6,022,315 A | 2/2000 | Iliff | |
| 6,113,540 A | 9/2000 | Iliff | |
| 6,129,668 A | * 10/2000 | Haynor et al. | 600/424 |
| 6,160,263 A | 12/2000 | Smith et al. | |
| 6,201,247 B1 | 3/2001 | Lutheran et al. | |
| 6,206,829 B1 | 3/2001 | Iliff | |
| 6,434,216 B1 | * 8/2002 | Maki et al. | 378/9 |

* cited by examiner

Primary Examiner—John R. Lee
Assistant Examiner—Christopher M. Kalivoda
(74) Attorney, Agent, or Firm—Armstrong Teasdale LLP; Carl B. Horton, Esq.

(57) ABSTRACT

A method for transporting a source pin in a Positron Emission Tomography (PET) system having a transmission ring includes aligning the transmission ring with a source pin within a storage device having a magnetic force holding the source pin in place, and moving the source pin from the storage device to the transmission ring using a magnetic force greater than the magnetic force of the storage device.

22 Claims, 3 Drawing Sheets

US 6,794,667 B2

SOURCE PIN LOADING METHODS AND APPARATUS FOR POSITRON EMISSION TOMOGRAPHY

BACKGROUND OF INVENTION

This invention relates generally to Positron Emission Tomography (PET) systems, and more particularly, to methods and apparatus for loading and storing radioactive source pins used in PET.

Radioactive source pins are used to calibrate PET detector systems. Source pins are also used to provide attenuation during system use or imaging. Because the pins are radioactive, they are stored in a shielded storage device when not in use. The storage device is structurally secure and shields the environment from radiation exposure from the radioactive source pin. The storage device is generally within the PET system. During use the source pin or pins are withdrawn from storage and placed in a rotatable transmission ring within a bore of the PET detector system.

After use, the pin or pins are returned to the storage device. Source pin transport time is a time period between initial removal of the source pin from the storage device to placement in the transmission ring. It is desirable to lessen source pin transport time to reduce potential non-beneficial radiation exposure. Because the shielding requirements limit the placement of the storage device automatic source pin handling is often complex and unreliable. It is therefore desirable to provide methods and apparatus that facilitates quick and reliable handling of the source pin including unloading the source pin from the storage device, transporting the pin and installation of the source pin within the transmission ring.

SUMMARY OF INVENTION

In one aspect, a method for transporting a source pin in a Positron Emission Tomography (PET) system having a transmission ring is provided. The method includes aligning the transmission ring with a source pin within a storage device having a magnetic force holding the source pin in place, and moving the source pin from the storage device to the transmission ring using a magnetic force greater than the magnetic force of the storage device.

In another aspect, an imaging system is provided. The imaging system includes a rotatable transmission ring, a storage device adjacent the transmission ring, and at least one source pin storable in the storage device. The storage device has a magnetic force holding the source pin in place. The system also includes a source of magnetic force on the transmission ring, the source is configured to move the source pin between the storage device and the transmission ring.

In still another aspect, an imaging system is provided. The system includes a rotatable transmission ring, a storage device adjacent the transmission ring, and a proximity sensor positioned to sense a presence of a source pin in the storage device.

In yet another aspect, a processor is provided. The processor is configured to align a transmission ring with a source pin within a storage device having a magnetic force holding the source pin in place, and move the source pin from the storage device to the transmission ring using a magnetic force greater than the magnetic force of the storage device.

In another aspect, a Positron Emission Tomography (PET) system is provided. The PET system includes a rotatable transmission ring, a storage device adjacent the transmission ring, and at least one source pin. The source pin is storable in the storage device, and the storage device has a magnetic force holding the source pin in place. The system also includes a proximity sensor positioned to sense a presence of the source pin within the storage device, and a source of magnetic force is on the transmission ring, the source is configured to move the source pin between the storage device and the transmission ring.

DETAILED DESCRIPTION

Figure 1:
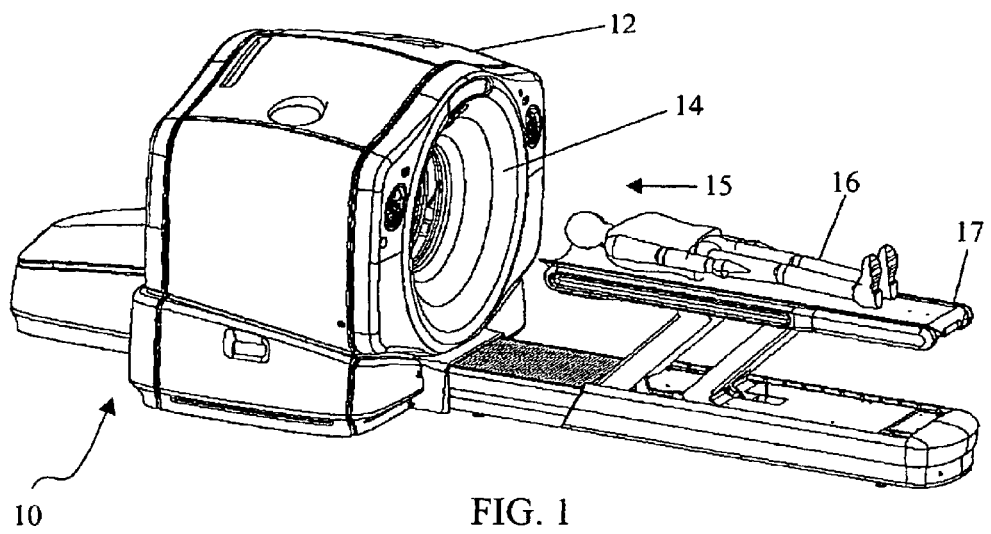
FIG. 1 is a pictorial view of an embodiment of a PET system.
Figure 2:
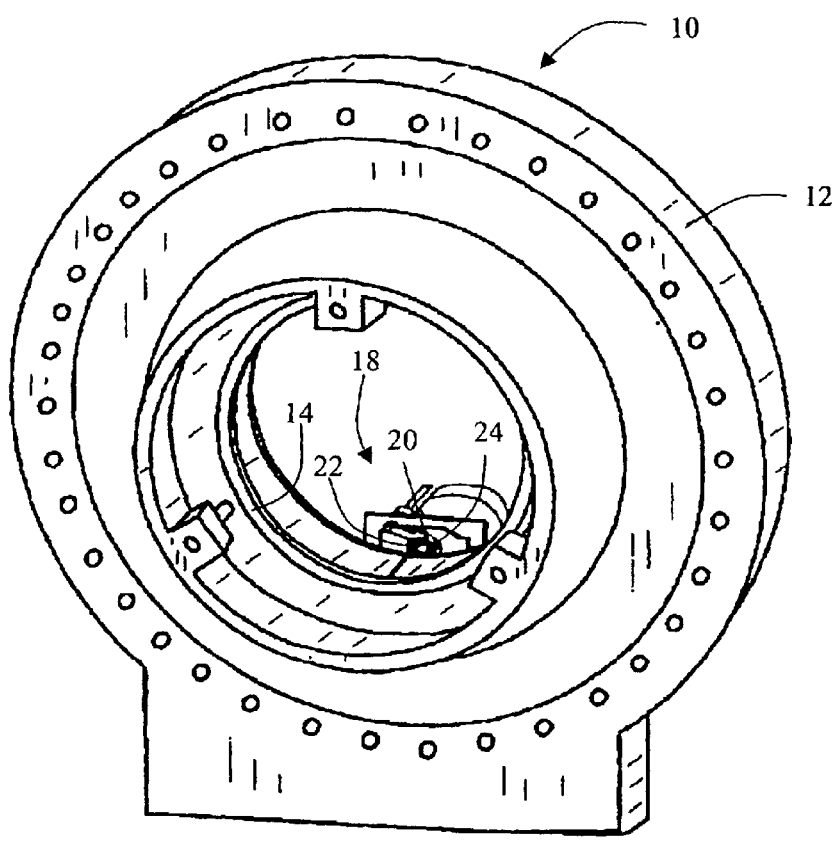
FIG. 2 is a perspective view of the gantry shown in FIG. 1.

Referring to FIGS. 1 and 2, a Positron Emission Tomography (PET) system 10 is shown including a gantry 12, a rotatable transmission ring 14 including a bore 15. In use, a patient 16 is positioned within bore 15 and PET system 10 is utilized to image portion or organs of patient 16 as is known in the art. Patient 16 is positioned on a table 17 which is translatable to move into and out of bore 15. System 10 also includes a storage device 18 for storing one or more radioactive source pins. In the exemplary embodiment, three source pins 20, 22, and 24 are stored in storage device 18. One radioactive source pin 20, 22, or 24 is removed from storage device 18 and installed in transmission ring 14 to calibrate PET system 10. In one embodiment, source pin 20, 22, or 24 is also removed from storage device 18 and installed in transmission ring 14 to provide attenuation measurements during patient scanning.

Figure 3:
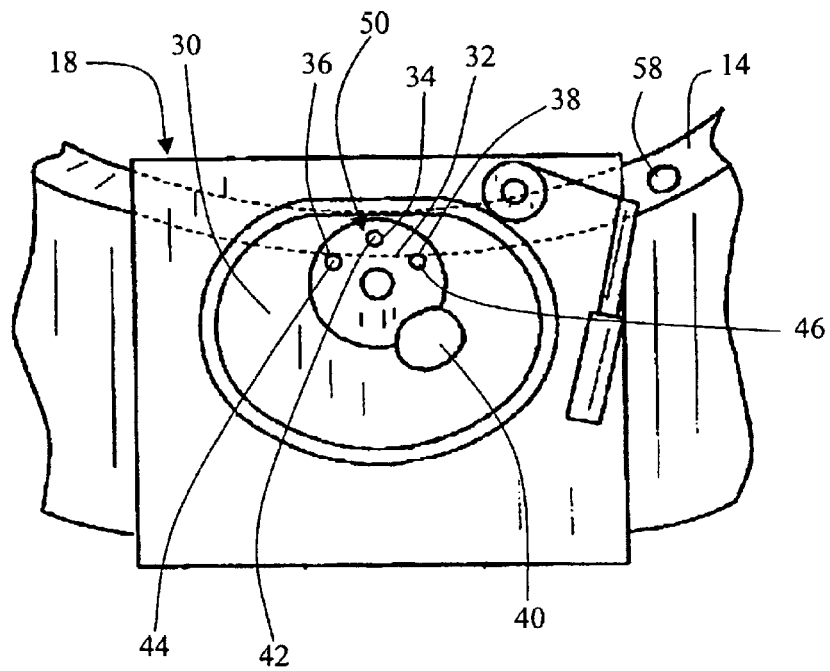
FIG. 3 is a partial rear view of the PET system of FIG. 1 including an embodiment of a storage device.

FIG. 3 is a partial rear view of PET system 10 including storage device 18. Storage device 18 includes primary shielding 30, a rotatable shielding cylinder 32, storage cavities 34, 36, and 38, and a rotating mechanism 40. Primary shielding 30 provides sufficient attenuation of radioactive source pins 20, 22, and 24 to protect the environment near the PET system 10, including personnel. Rotatable shielding cylinder 32 is within primary shielding 30 and is selectively rotated or indexed. Storage cavities 34, 36, and 38 have cylindrical cross-sectional profiles that are substantially concentric with respect to respective axes 42, 44, and 46. Each storage cavity 34, 36, or 38 is sized to contain a portion of one source pin 20, 22, or 24. In the exemplary embodiment, rotatable shielding cylinder 32 is indexed by rotating mechanism 40 to four positions, including a storage position (not illustrated), and an access position 50 for each storage cavity 34, 36, and 38. When rotatable shielding cylinder 32 is indexed to the storage position, rotatable shielding cylinder 32 is positioned such that storage cavities 34, 36, and 38 are substantially centered within primary shielding 30. FIG. 3 illustrates storage cavity 34 in access position 50 such that axis 42 is aligned substantially perpendicular to transmission ring 14 and co-axially with one of a plurality of receiver openings 58 in transmission ring 14. In one embodiment, receiver openings 58 include magnetic material to secure source pins 20, 22, or 24. Transmission ring 14 is also indexed to ensure receiver openings 58 are aligned to access position 50. Control of rotating mechanism 40, transmission ring 14 rotation, and operation of PET system 10 are controlled as is known in the art.

Figure 4:
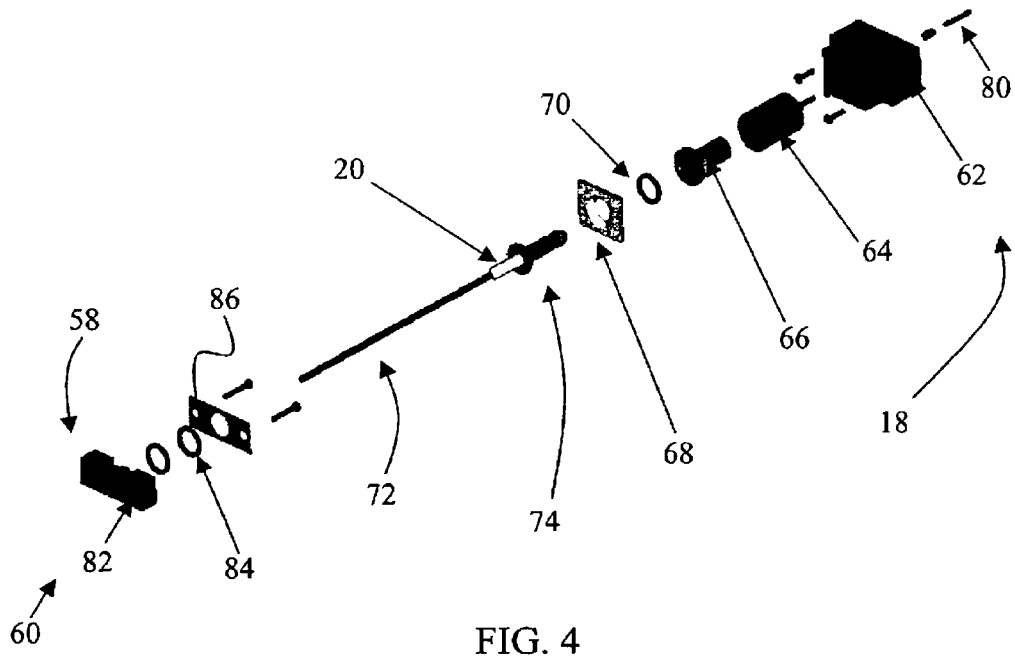
FIG. 4 is an exploded perspective view of one storage cavity of the storage device shown in FIG. 3 and a receiver opening together forming a radioactive source pin transport system.

FIG. 4 is an exploded perspective view of one storage cavity 34 of storage device 18 and receiver opening 58 together forming a radioactive source pin transport system 60. System 60 includes a housing 62 and an electromagnet 64 positioned within housing 62. An electromagnet core 66 is positioned within electromagnet 64. A magnetic cover 68 maintains a ring magnet 70 against electromagnet core 66. Source pin 20 includes a radiation portion 72 and a non-radiation portion 74. A proximity sensor 80 is positioned to detect a presence of source pin 20 within housing 62. In one embodiment, proximity sensor 80 is a normally open Negative-Positive-Negative (NPN) inductive sensor. Also, in an exemplary embodiment, proximity sensor 80 and source pin 20 are axially aligned such that sensor 80 axially senses a presence of source pin 20 within housing 62. Pin transport system 60 also includes a transmission ring magnetic pin holder 82 that is positioned on transmission ring 14. At least one magnet 84 is positioned within holder 82 and maintained in place with a holder cover 86. In one embodiment, magnet 84 includes two ring shaped permanent magnets each having a force of about 5.34 Newtons (N) providing a combined force of about 10.67 N. Additionally, ring magnet 70 also has a force of 5.34 N and is similarly sized to magnet 84, and because magnets 70 and 84 are thus interchangeable, construction of system 60 is simplified over designs using magnets of different strengths and/or sizes.

Figure 5:
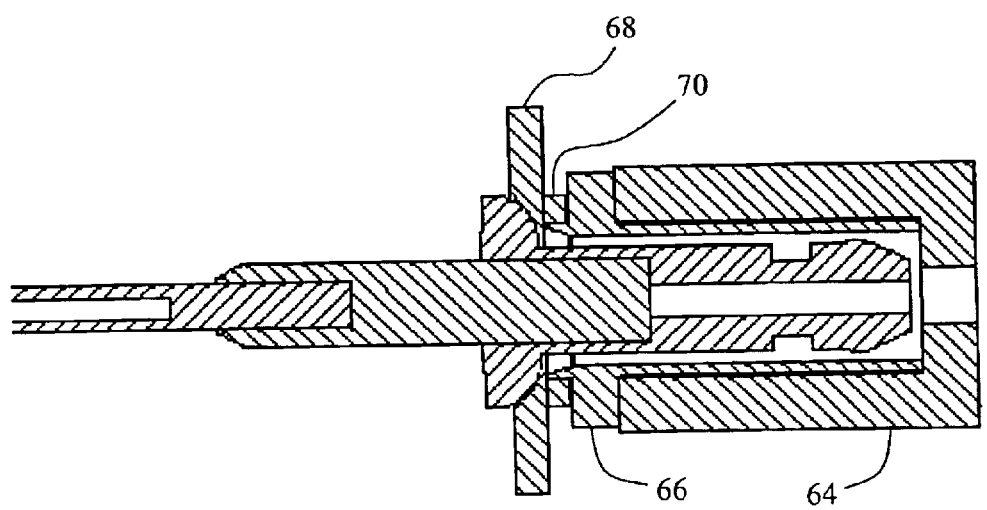
FIG. 5 is a cut away view of the source pin shown in FIG. 2 positioned at least partially within the electromagnet core positioned within the electromagnet shown in FIG. 4.
Figure 6:
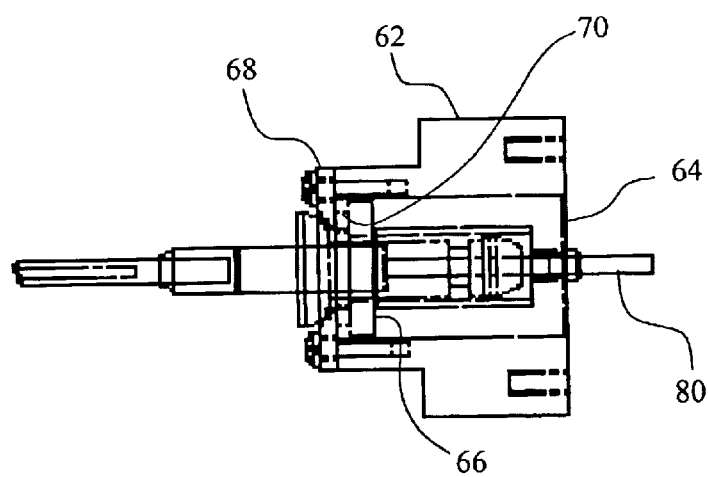
FIG. 6 is a partially cut away view of the sensor shown in FIG. 4 positioned to sense a presence of the source pin within the housing shown in FIG. 4 in accordance with one embodiment.

FIG. 5 is a cut away view of source pin 20 (shown in FIG. 2) positioned at least partially within electromagnet core 66 positioned within electromagnet 64 (shown in FIG. 4). FIG. 6 is a partially cut away view of sensor 80 (shown in FIG. 4) positioned to sense a presence of source pin 20 (shown in FIG. 2) within housing 62 (shown in FIG. 4) in accordance with one embodiment.

In use of system 60, radio-active source pin 20 is released from storage device 18 when there is a net force along the axis centerline of source-pin 20 that is pointing towards magnetic pin holder 82 on transmission ring 14. This state is reached when electromagnet 64 is de-energized and the only pull force towards storage device 18 is that of permanent magnet 70 positioned inside housing 62, in this situation a pull force of transmission ring magnetic pin holder 82 on transmission ring 14 of about 2.4 Pound-force (lbf) (10.67 N) is approximately twice of that of permanent magnet 70 (about 1.2 lbf, 5.34 N) inside housing 62. Consequently, a net force exists of about 1.2 lbf (5.34 N) towards magnetic pin holder 82, and hence source-pin 20 is accelerated over a small distance to end up positioned flush with transmission ring magnetic pin holder 82.

Additionally, system 60 allows for an easy removal of source pin 20 from transmission ring 14. During this removal process, a reverse logic is utilized.

Conversely, in this removal process, electromagnet 64 is energized, which produces a nominal pull force of approximately 5.3 lbf (23.6 N). The orientation of permanent magnet 70 inside housing 62 is such that the cumulative effect of the total pull force is the vectorial sum of permanent magnet 70 and a electromagnet force of attraction from electromagnet 64, thus resulting in a net pull force of approximately 4.1 lbf (18.24 N). This force accelerates source-pin 20 towards housing 62 over a small distance between transmission ring 14 and storage device 18 and maintains source-pin 20 in a storage position within housing 62. Housing 62 is rotated away from transmission ring magnetic pin holder 82, and electromagnet 64 is de-energized, and source-pin 20 is maintained within housing 62 solely via permanent magnet 70 in housing 62.

In one embodiment, transmission ring 14 is aligned with source pin 20 within storage device 18 wherein storage device has at least two magnetic forces including a permanent magnet force of at least about 5.34 Newtons (N) and an electromagnet force of at least about 23.6 N holding the source pin in place. Source pin 20 is moved by de-energizing the electromagnet force and moving the source pin from the storage device to the transmission ring using a magnetic force of at least about 10.67 N. These herein described forces have empirically shown to be highly effective for accurately and quickly moving source pin 20 back and forth between transmission ring 14 and storage device 18. Additionally, in one embodiment, system 10 includes a processor (not shown) programmed to perform the functions herein described. It is contemplated that the benefits of the invention accrue to embodiments employing a programmable circuit other than those known in the art as processors, therefore, as used herein, the term processor is not limited to just those integrated circuits referred to in the art as processors, but broadly refers to computers, processors, microcontrollers, microcomputers, programmable logic controllers (PLCs), application specific integrated circuits (ASICs), field programmable gate array (FPGA), and other programmable circuits. Additionally, although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center. The benefits also accrue to micro PET systems which are sized to study lab animals as opposed to humans.

Also provided herein is a Fail Safe Mode. The fail safe mode is to continuously energize electromagnet 64 during source-pin transit and only de-energize electromagnet 64 during the above described pin-release process. In this mode, permanent magnet 70 inside housing 62 acts as a fail safe feature, such that if electromagnet 64 lost power, then housing 62 is still capable of retaining source-pin 20 via the pull force of magnet 70.

The herein described methods and apparatus facilitate an increase in component and system reliability, since the radio-active source pin exposure and storage process is of importance relative to system operation and up-time. This is at least partially due to the reason that typical software operating on PET systems is configured such that the system will stop functioning and log a system error if this fault occurs. The herein described methods and apparatus facilitate a secure and reliable means of grabbing and releasing the source-pin. The methods and apparatus herein described also facilitate a cost savings based on production costs. System 60 utilizes no moving parts, and uses an electrical signal as a means of latching radioactive source-pin 20, and verses known mechanical transport systems that utilize moving components which wear due to cyclical motion, system 60 provides a long lasting and cost effective method to transport source pins between a transmission ring and a storage device.

PET system embodiments of the present invention are cost-effective and highly reliable. A storage device includes a rotatable shielding cylinder that rotates a selected storage cavity to an access position that is aligned with a receiver opening in a transmission ring. A source loader linearly transports a source pin and installs the source pin in the transmission ring. Similarly, the source pin is removed from the transmission ring and returned to the storage cavity. The rotatable shielding cylinder then rotates to a storage position. As a result, embodiments of the present invention facilitate quick and reliable handling of radioactive source pins.

While the invention has been described in terms of various specific embodiments, those skilled in the art will recognize that the invention can be practiced with modification within the spirit and scope of the claims.

What is claimed is:

1. A method for transporting a source pin in a Positron Emission Tomography (PET) system having a transmission ring, said method comprising:
    aligning the transmission ring with a source pin within a storage device having a magnetic force holding the source pin in place; and
    moving the source pin from the storage device to the transmission ring using a magnetic force greater than the magnetic force of the storage device.

2. A method in accordance with claim 1 wherein said aligning the transmission ring comprises aligning the transmission ring with a source pin within a storage device having at least two magnetic forces including a permanent magnet force and an electromagnet force holding the source pin in place, said moving the source pin comprises moving the source pin from the storage device to the transmission ring using a magnetic force greater than the magnetic force of the permanent magnet and less than the combined magnetic force of the electromagnet and the permanent magnet.

3. A method in accordance with claim 1 wherein said aligning the transmission ring comprises aligning the transmission ring with a source pin within a storage device having at least two magnetic forces including a permanent magnet force and an electromagnet force holding the source pin in place, said moving the source pin comprises moving the source pin from the storage device to the transmission ring using a magnetic force at least twice greater than the magnetic force of the permanent magnet and less than the combined magnetic force of the electromagnet and the permanent magnet.

4. A method in accordance with claim 1 wherein said aligning the transmission ring comprises aligning the transmission ring with a source pin within a storage device having at least two magnetic forces including a permanent magnet force of at least about 5.34 Newtons (N) and an electromagnet force of at least about 23.6 N holding the source pin in place, said moving the source pin comprises:
    de-energizing the electromagnet force; and
    moving the source pin from the storage device to the transmission ring using a magnetic force of at least about 10.67 N.

5. A method in accordance with claim 1 further comprising moving the source pin from the transmission ring to the storage device using the magnetic force of the storage device.

6. A method in accordance with claim 5 further comprising sensing a presence of the source pin in the storage device using a proximity sensor.

7. A method in accordance with claim 6 wherein said sensing a presence of the source pin comprises sensing a presence of the source pin in the storage device using a proximity sensor comprising a normally open Negative-Positive-Negative (NPN) inductive sensor.

8. A method in accordance with claim 6 wherein said sensing a presence of the source pin comprises axially sensing a presence of the source pin in the storage device using a proximity sensor.

9. A method in accordance with claim 8 wherein said axially sensing a presence of the source pin comprises axially sensing a presence of the source pin in the storage device using a proximity sensor comprising a normally open Negative-Positive-Negative (NPN) inductive sensor.

10. An imaging system comprising:
    a rotatable transmission ring;
    a storage device adjacent said transmission ring;
    at least one source pin storable in said storage device, said storage device having at least two magnetic forces including a permanent magnet force and an electromagnet force holding said source pin in place; and
    a source of magnetic force on said transmission ring, said source configured to move said source pin between said storage device and said transmission ring.

11. A system in accordance with claim 10 wherein said source of magnetic force on said transmission ring comprises a magnetic force greater than the magnetic force of said storage device permanent magnet and less than a combined magnetic force of said storage device electromagnet and said storage device permanent magnet.

12. A system in accordance with claim 11 wherein said source of magnetic force on said transmission ring comprises a permanent magnet.

13. An imaging system comprising:
    a rotatable transmission ring;
    a storage device adjacent said transmission ring, said storage device comprises a magnetic force holding a source pin in place; and
    a proximity sensor positioned to sense a presence of the source pin in said storage device, wherein said rotatable transmission ring comprises a source of magnetic force stronger than said storage device magnetic force and configured to move said source pin between said storage device and said transmission ring.

14. A system in accordance with claim 13 wherein said proximity sensor comprises a normally open Negative-Positive-Negative (NPN) inductive sensor.

15. A processor configured to:
    align a transmission ring with a source pin within a storage device having a magnetic force holding the source pin in place; and
    move the source pin from the storage device to the transmission ring using a magnetic force greater than the magnetic force of the storage device.

16. A processor in accordance with claim 15 further configured to:
    align the transmission ring with a source pin within a storage device having at least two magnetic forces including a permanent magnet force and an electromagnet force holding the source pin in place; and
    move the source pin from the storage device to the transmission ring using a magnetic force greater than the magnetic force of the permanent magnet and less than the combined magnetic force of the electromagnet and the permanent magnet.

17. A processor in accordance with claim 15 further configured to:
- align the transmission ring with a source pin within a storage device having at least two magnetic forces including a permanent magnet force and an electromagnet force holding the source pin in place; and
- move the source pin from the storage device to the transmission ring using a magnetic force at least twice greater than the magnetic force of the permanent magnet and less than the combined magnetic force of the electromagnet and the permanent magnet.

18. A processor in accordance with claim 15 further configured to:
- align the transmission ring with a source pin within a storage device having at least two magnetic forces including a permanent magnet force of at least about 5.34 Newtons (N) and an electromagnet force of at least about 23.6 N holding the source pin in place;
- de-energize the electromagnet force; and
- move the source pin from the storage device to the transmission ring using a magnetic force of at least about 10.67 N.

19. A processor in accordance with claim 15 further configured to receive a signal from a proximity sensor indicative of a presence of the source pin in the storage device.

20. A processor in accordance with claim 15 further configured to receive a signal from a normally open Negative-Positive-Negative (NPN) inductive sensor indicative of a presence of the source pin in the storage device.

21. A processor in accordance with claim 18 further configured to receive a signal from a normally open Negative-Positive-Negative (NPN) inductive sensor indicative of a presence of the source pin in the storage device.

22. A Positron Emission Tomography (PET) system comprising:
- a rotatable transmission ring;
- a storage device adjacent said transmission ring;
- at least one source pin sized to be storable in said storage device, said storage device having a magnetic force holding said source pin in place;
- a proximity sensor positioned to sense a presence of said source pin within said storage device; and
- a source of magnetic force on said transmission ring stronger than said storage device magnetic force, said transmission ring source configured to move said source pin between said storage device and said transmission ring.

* * * * *